United States Patent
Thramann

(10) Patent No.: US 8,075,581 B2
(45) Date of Patent: Dec. 13, 2011

(54) MUSCLE SAVING DEVICE AND METHOD

(75) Inventor: Jeffery Thramann, Longmont, CO (US)

(73) Assignee: Lanx, Inc., Broomfield, CO (US)

( * ) Notice: Subject to any disclaimer, the term of this patent is extended or adjusted under 35 U.S.C. 154(b) by 1344 days.

(21) Appl. No.: 11/135,685

(22) Filed: May 24, 2005

(65) Prior Publication Data

US 2006/0276799 A1    Dec. 7, 2006

(51) Int. Cl.
*A61M 29/00*    (2006.01)

(52) U.S. Cl. ........... 606/191; 606/90; 604/104; 600/201

(58) Field of Classification Search ............. 606/90, 606/103, 191; 604/104; 600/208, 201
See application file for complete search history.

(56) References Cited

U.S. PATENT DOCUMENTS

| | | | |
|---|---|---|---|
| 4,895,564 A * | 1/1990 | Farrell | ........................ 604/164.1 |
| 5,976,146 A | 11/1999 | Ogawa et al. | |
| 6,793,656 B1 | 9/2004 | Mathews | |
| 6,916,330 B2 | 7/2005 | Simonson | |
| 2003/0083688 A1* | 5/2003 | Simonson | ..................... 606/191 |
| 2005/0004593 A1 | 1/2005 | Simonson | |
| 2006/0047296 A1* | 3/2006 | Embry et al. | ................. 606/191 |

OTHER PUBLICATIONS

International Searching Authority, International Search Report and Written Opinion for Application No. PCT/US2008/080931, Dec. 23, 2008.*

* cited by examiner

*Primary Examiner* — Eduardo C Robert
*Assistant Examiner* — Julianna N Harvey
(74) *Attorney, Agent, or Firm* — Holland & Hart

(57) ABSTRACT

A method, kit, and system to separate muscle fiber prior to threading pedicle screws. The kit and system include at least one dilator that is sized and shaped with a leading edge to expand and separate muscle fibers between the first and second pedicles. The dilator(s) expose the surgical area by separating the muscle fiber prior to threading the pedicle screws. Because the muscle fiber is spread, it does not need to be cut to place rods, which facilitates minimally invasive surgical methods.

9 Claims, 4 Drawing Sheets

MUSCLE SAVING DEVICE AND METHOD

FIELD OF THE INVENTION

The present invention relates to a device useful in saving muscle during surgery and, more particularly, to a device useful in minimally invasive spinal surgery to avoid or reduce cutting muscle fiber along the spine.

BACKGROUND OF THE INVENTION

Minimally invasive surgery is preferable to non-minimally invasive surgery. Conventionally, many spinal surgeries include the placement of implants through minimally invasive techniques.

However, conventional methods and devices still require cutting muscle tissue about the spine decreasing the effectiveness of minimally invasive procedure. For example, and much abbreviated from the actual procedure, when placing a rod and two pedicle screws, a surgeon may use a navigation system to locate where the surgeon want to place the screw. The surgeon inserts a guide wire and dilator to the located point and threads the pedicle screw into the pedicle. The surgeon repeats the process for the second pedicle screw. Once the screws are placed, a surgical incision is made to provide access such that a spinal rod can be inserted between the screws. Except by happenstance, the surgeon needs to cut through muscle fiber to insert the spinal rod. Cutting the muscle reduces the effectiveness of the minimally invasive surgery.

It would be advantageous to develop a device and method that would drastically reduce the need to cut muscle fiber during minimally invasive surgical procedures.

SUMMARY OF THE INVENTION

To attain the advantages and in accordance with the purpose of the invention, as embodied and broadly described herein, a method for saving muscle during surgery is provided. The method comprising the steps of locating a first place on a first pedicle to thread a first pedicle screw and inserting a first guide wire at the first place. Placing a first dilator over the first guide wire to separate muscle fiber and expanding and inserting at least one additional dilator over the first dilator to separate the muscle fiber from the first pedicle to a second pedicle. The at least one additional dilator or a subsequent final extending from the first pedicle to the second pedicle exposing a surgical area. The second guide wire can than be placed to thread the second pedicle screw such that the first place and the second place reside in the surgical area in the muscle fiber.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
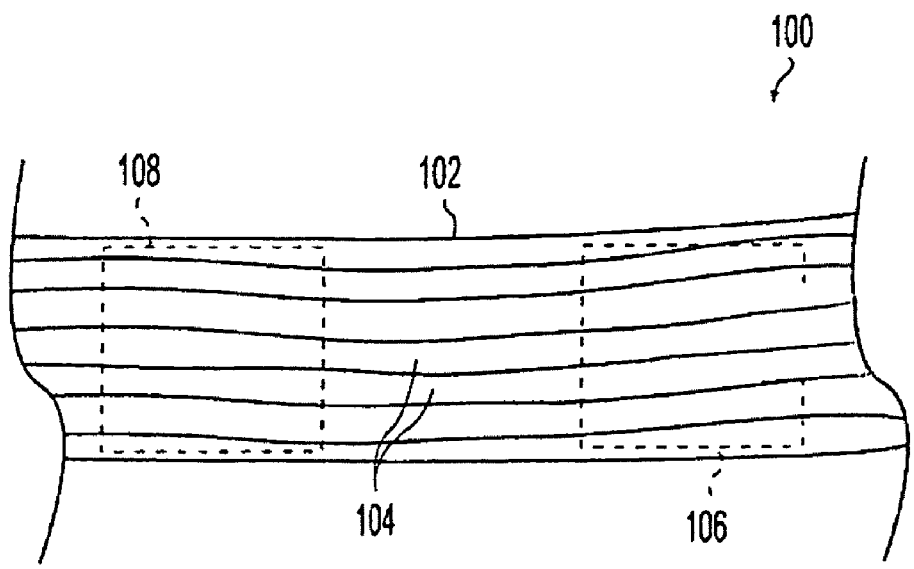
FIG. 1 is a top elevation view of muscle fiber over a superior pedicle and an inferior pedicle.
Figure 2:
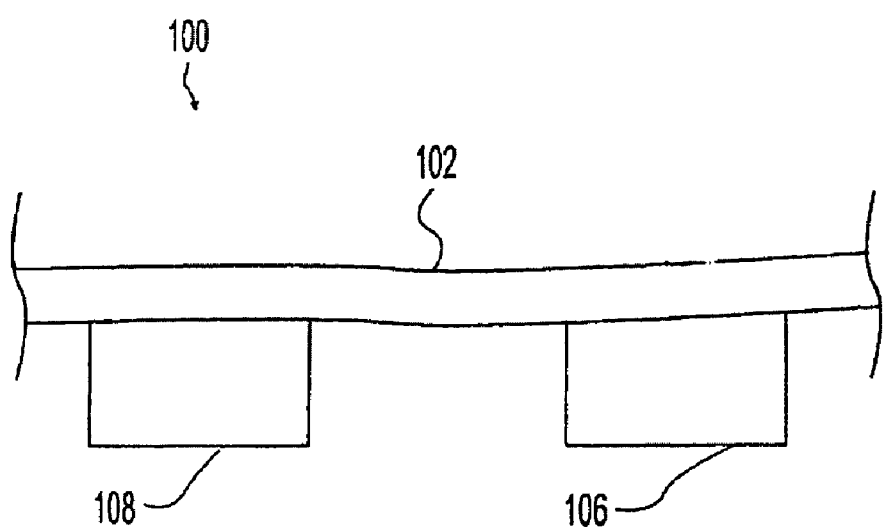
FIG. 2 is a side elevation view of FIG. 1.
Figure 3:
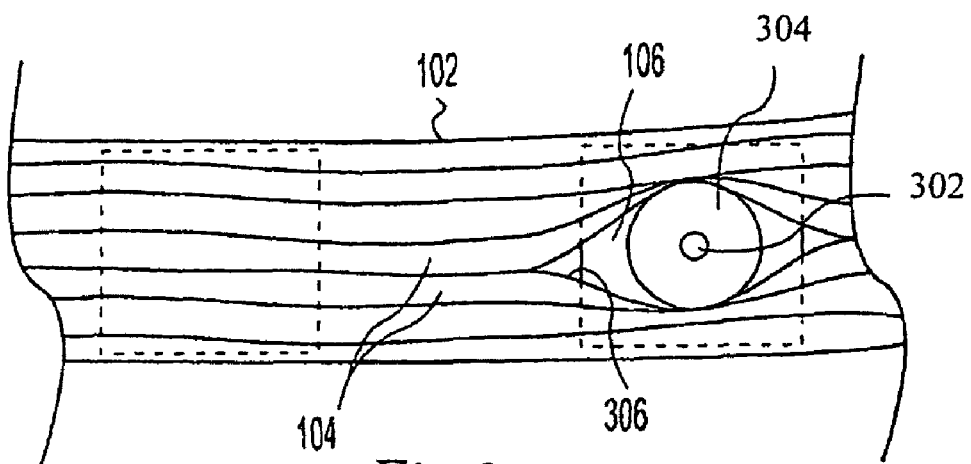
FIG. 3 is a top elevation view of muscle fiber with a guide wire and dilator placed separating muscle fiber consistent with an embodiment of the present invention.

The present invention will now be described with reference to FIGS. 1 to 7. Referring first to FIGS. 1 and 2, a posterior view and a lateral view of a spinal segment 100 is shown. The Figures are not drawn to scale and only show those potions of the anatomy necessary to understand the present invention. Segment 100 has a layer of muscle 102 comprising substantially parallel muscle fibers 104. Muscle 102 resides posterior to a superior pedicle 106 and an inferior pedicle 108.

To implant a rod between superior pedicle 106 and 108, as mentioned above and with reference to FIG. 3, a surgeon would locate and place a guide wire 302 using conventional navigation technologies on superior pedicle 106, for example, although the surgeon could start with inferior pedicle 108. Next, a dilator 304 is inserted over the guide wire to provide surgical access through the skin. Dilator 304 expands muscle fibers 104 making an exposure area 306 exposing pedicle 106. Conventionally, at this point, a pedicle screw would be threaded over guide wire 302 and dilator 304 would be removed.

Figure 4:
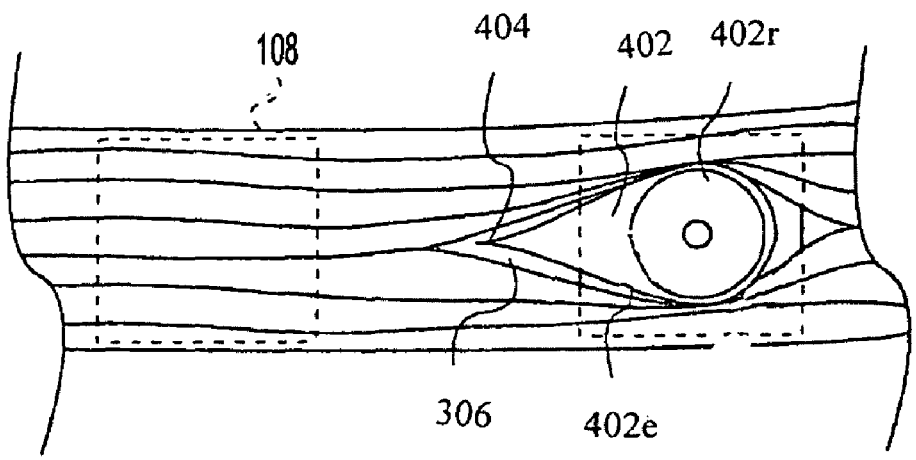
FIG. 4 is a top elevation view of FIG. 3 with a subsequent dilator separating a portion of muscle fiber extending between superior pedicle and inferior pedicle.

Instead of threading a screw and removing dilator 304, the present invention comprises at least one additional dilator, and typically a series of dilators inserted over initial dilator 304. Referring now to FIG. 4, a second dilator 402 is shown inserted over first dilator 304. Second dilator 402 expands exposure area 306 towards the next pedicle, which in this case is inferior pedicle 108. While second dilator 402 is shown having a leading edge 404 giving it a knife, tear drop, or wedge shape, the successive dilators could be any shape including conventional circular shapes. However, it is believed a wedge shape will assist in spreading the muscle fibers. Also, instead of successive dilators, a means of expanding a first dilator is possible. Such, for example, use of a gas to pressurize the dilator and designing the dilator so it can expand in only the desire direction. Alternatively, the dilator may be made out of an expandable material, such as, a shaped memory alloy that can be caused to expand on activation. To be expandable in the desired direction, dilator 402, for example, may comprise at least one substantially rigid portion $402_r$ and at least one substantially elastic portion $402_e$. The at least one substantially rigid portion $402_r$ would reside at least at the portion of dilator 402 that was not to expand. Leading edge 404 may also be relatively rigid if desired to facilitate muscle fiber separation. While the example above is described with a second dilator, first dilator 304 could be expandable making dilator 402 unnecessary and optional.

The dilators according to the present invention could be place over the guide wire and/or screw as described above.

Additionally, extenders may or may not be used to assist the surgeon in placement of the dilators as desired.

Figure 5:
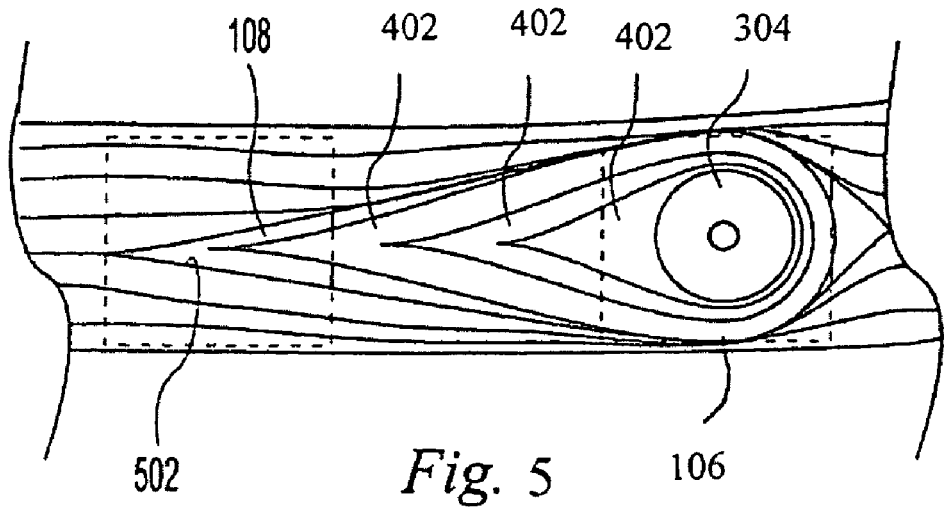
FIG. 5 is a top elevation view of FIG. 3 with a subsequent dilator separating a portion of muscle fiber extending between superior pedicle and inferior pedicle.

Referring now to FIG. 5, a segment 100 is shown with a series of dilators 402 installed over first dilator 304. A sufficient number of dilators 402 have been installed such that inferior pedicle 108 is exposed in a second exposure area 502. While all dilators 402 are shown as successively inserted, internal dilators 402 can be removed as desired.

Figure 6:
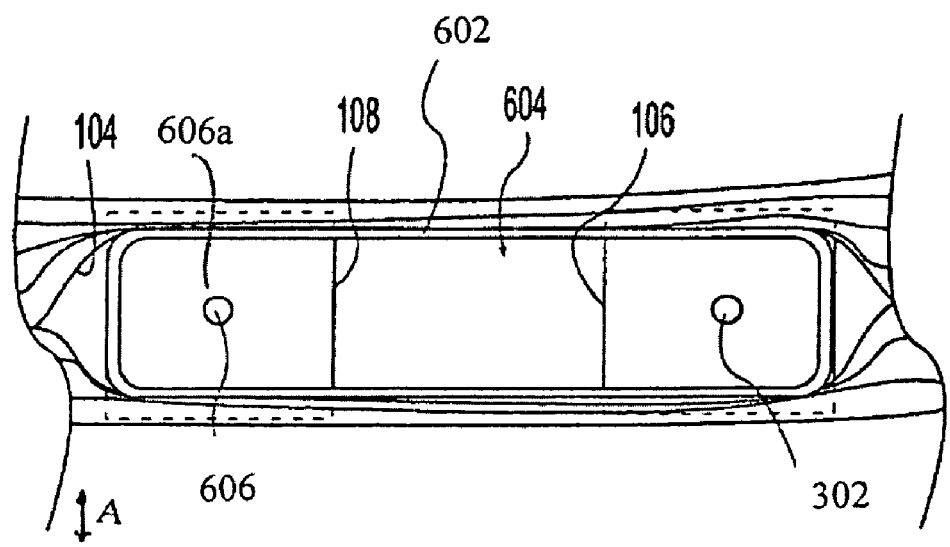
FIG. 6 is a top elevation view of FIG. 3 where the muscle fiber is separated exposing the surgical site without needlessly cutting muscle fiber.

Referring now to FIG. 6, once the appropriate portion of pedicle 108 is exposed, a final dilator 602 is inserted and the dilators 402 are removed providing a surgical access 604 between superior pedicle 106 and inferior 108 along a particular muscle fiber. Guide wires 302 and 606 are located, and pedicles screws can be threaded over guide wires 302 and 606 in a conventional manner. Muscle fiber 104 moves relatively freely in a lateral direction A. Thus, location of guide wires and eventually the pedicle screws can be aligned properly.

Because fibers 104 were spread from superior pedicle 106 to inferior pedicle 108, a rod can be inserted without cutting across muscle fibers 104. The rod would be installed using any conventional method.

Figure 7:
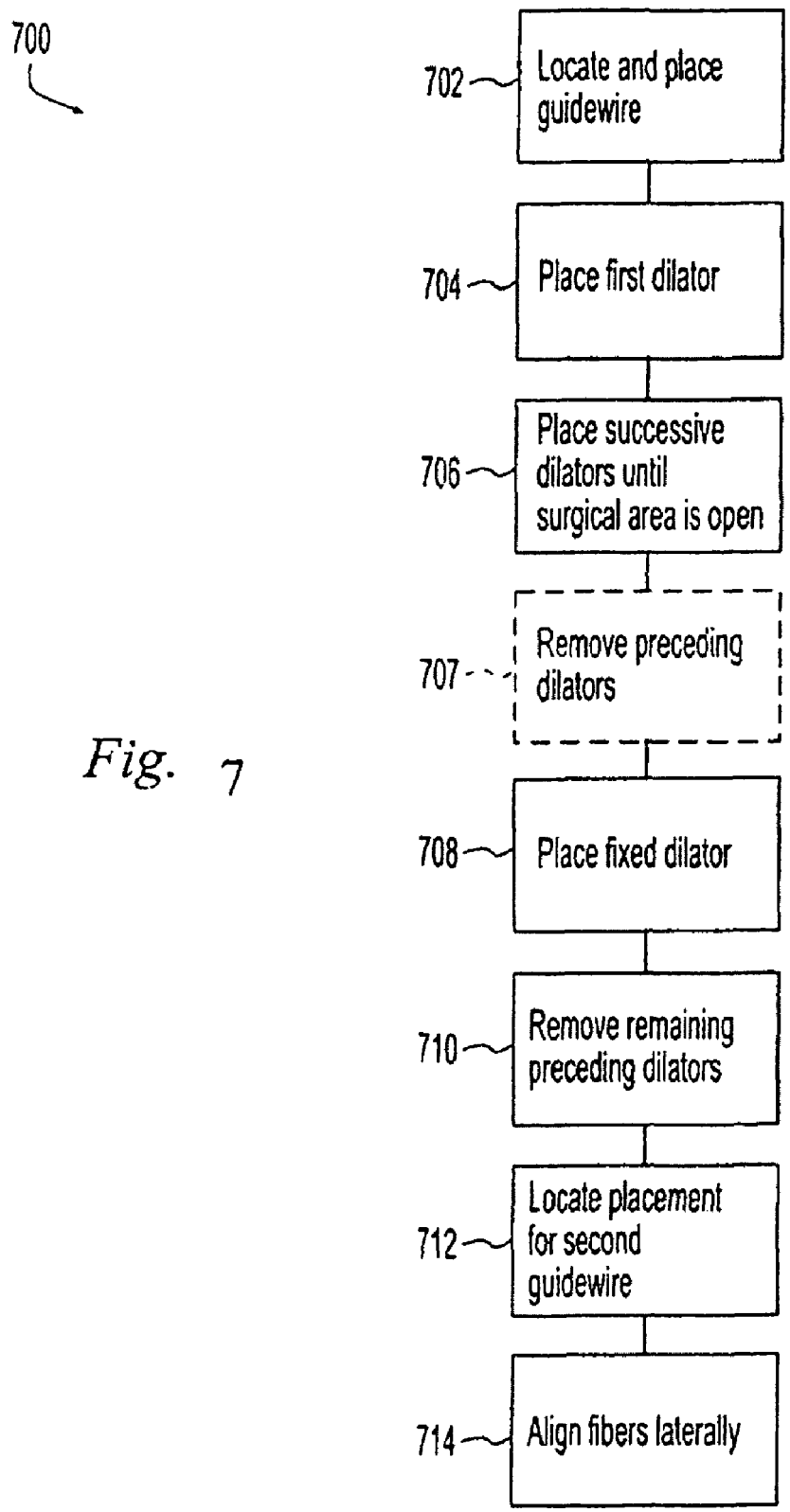
FIG. 7 is a flowchart outlining possible procedural steps useful in using the muscle saving device consistent with the present invention.

For completeness, FIG. 7 is a representative flowchart 700 of using the present invention. First, a surgeon locates a pedicle screw placement on a first pedicle and inserts a guide wire, step 702. Next, the surgeon places a dilator over the guide wire, step 704. A series of dilators are inserted to spread the muscle fiber without cutting the fiber from a first pedicle to a second pedicle, step 706. Successive dilators are external and larger than preceding dilators. Step 706 is repeated until the surgical area between pedicles is exposed. Once the surgical area is exposed, a final dilator is placed extending between first pedicle and second pedicle and exposing a surgical area, step 708. To the extent expandable dilators are used, step 706 would be replaced with a step of expanding the dilator to spread the muscle fiber until the surgical area between pedicles is exposed. Moreover, the final dilator can be the expandable dilator and/or the final dilator that actually spreads muscle. The preceding dilators are removed, step 710. A second pedicle screw placement is located, step 712. Finally, the muscle fibers are laterally aligned such that the surgical area encompasses the first and second pedicle screw placement areas, step 714. Notice, location of the second pedicle screw can be done before or after dilation of the muscle fiber. Moreover, and optionally, preceding internal dilators can be removed subsequent to placement of an external dilator, step 707.

Notice, once the surgical area is exposed, if the final dilator has an access $606_a$ for the second guide wire, such as a hole or punch sport, the guide wire can be inserted using surgical navigation techniques through the dilator access $606_a$. The second pedicle screw, with or without extenders, could be threaded, before or after the incision. Notice, because the muscle fiber is spread prior to the incision, less or no muscle fiber needs to be cut. Cutting less muscle fiber increases the effectiveness of minimally invasive procedures.

An embodiment of the present invention and many of its improvements have been described with a degree of particularity. It should be understood that this description has been made by way of example, and that the invention is defined by the scope of the following claims.

I claim:

1. A muscle saving kit useful for minimally invasive surgical procedures, comprising:
    at least two dilators having a longitudinal axis, the at two dilators having a hollow generally cylindrical body extending parallel to the longitudinal axis, a first portion of the body and a second portion of the body disposed in opposition to one another in a direction orthogonal to the longitudinal axis, the first portion of the body defining a continuously curved outer surface the second portion of the body tapering to a radially projecting narrow edge formed on only one side of the body, the radially projecting narrow edge being operative upon insertion of the at least two dilators, in the direction of the longitudinal axis, between muscle fibers, to separate the muscle fibers in a direction perpendicular to the longitudinal axis, and at least one of the at least two dilators being sized differently than another one of the at least two dilators adapted for consecutive placement as a set of dilators.

2. The kit of claim 1, wherein the at least two dilators comprises a plurality of successively sized dilators where each of the successively sized dilators is larger than the preceding dilator and each dilator is non-expandable.

3. A muscle saving kit useful for minimally invasive surgical procedures, comprising:
    at least two muscle separating dilators having a longitudinal axis, the at least two muscle separating dilators having a hollow generally cylindrical body extending parallel to the longitudinal axis, a first portion of the body and a second portion of the body disposed in opposition to one another in a direction orthogonal to the longitudinal axis, the first portion of the body defining a continuously curved outer surface, the second portion of the body tapering to a radially projecting tapered leading surface formed on only one side of the body, the tapered leading surface being operative upon insertion of the at least two muscle separating dilators, in the direction of the longitudinal axis, between muscle fibers, to separate the muscle fibers in a direction perpendicular to the longitudinal axis, and at least one of the at least two dilators being sized differently than another one of the at least two dilators adapted for consecutive placement as a set of dilators.

4. The muscle saving kit of claim 3, wherein the at least two muscle separating dilators comprises a plurality of dilators.

5. The muscle saving kit of claim 3, wherein the leading surfaces of the at least two muscle separating dilators are a leading edge to facilitate separation of muscle fibers.

6. The muscle saving kit of claim 3, wherein the at least two muscle separating dilators are expandable in a direction from the first pedicle to the second pedicle.

7. A muscle saving kit useful for surgical procedures, comprising:
    at least two muscle separating dilators,
    the at least two muscle separating dilators having a longitudinal axis, the at least two muscle separating dilators having a hollow generally cylindrical body extending parallel to the longitudinal axis, a first portion of the body and a second portion of the body disposed in opposition to one another in a direction orthogonal to the longitudinal axis, the first portion of the body defining a continuously curved outer surface, the second portion of the body tapering to a radially projecting narrow edge formed on only side of the body, the radially projecting narrow edge being operative upon insertion of the at least two muscle separating dilators, in the direction of the longitudinal axis, between muscle fibers, to separate the muscle fibers in a direction perpendicular to the longitudinal axis such that the radially projecting narrow edge for separating muscle fibers is adapted to move between the muscle fibers between a first portion of a surgical site and a second portion of the surgical site such that a surgical area is exposed, and at least one of the at least two dilators being sized differently than another one of the at least two dilators adapted for consecutive placement as a set of dilators; and means for maintaining the open surgical area between the first portion of the surgical site and the second portion of the surgical site to provide surgical access to the surgical area, whereby the muscle fibers may be separated by the at least two muscle separating dilators without cutting or tearing the muscle fiber.

8. The muscle saving kit of claim 7 wherein the means for maintaining the open surgical area comprises a final dilator shaped to maintain the surgical area.

9. The muscle saving kit of claim 7 wherein the narrow leading edge is selected from the group of leading edges consisting of: a knife shape, a tear drop shape, or a wedge shape.

* * * * *